US009028447B2

(12) United States Patent
Baid (10) Patent No.: US 9,028,447 B2
(45) Date of Patent: May 12, 2015

(54) NEEDLE PROTECTOR ASSEMBLY (75) Inventor: Rishi Baid, New Delhi (IN)

(73) Assignee: Poly Medicure Limited, Haryana (IN)

( * ) Notice: Subject to any disclaimer, the term of this patent is extended or adjusted under 35 U.S.C. 154(b) by 0 days.

(21) Appl. No.: 13/821,550

(22) PCT Filed: Sep. 27, 2010

(86) PCT No.: PCT/IB2010/054334
§ 371 (c)(1),
(2), (4) Date: Mar. 7, 2013

(87) PCT Pub. No.: WO2012/032378
PCT Pub. Date: Mar. 15, 2012

(65) Prior Publication Data
US 2013/0184657 A1 Jul. 18, 2013

(30) Foreign Application Priority Data

Sep. 7, 2010 (IN) .............. 2124/DEL/2010

(51) Int. Cl.
*A61M 25/06* (2006.01)
*A61M 5/00* (2006.01)
*A61M 5/32* (2006.01)

(52) U.S. Cl.
CPC .............. *A61M 5/00* (2013.01); *A61M 5/3243* (2013.01); *A61M 5/3271* (2013.01); *A61M 25/0631* (2013.01); *A61M 25/0637* (2013.01); *A61M 2005/3247* (2013.01)

(58) Field of Classification Search
CPC . A61M 5/0158; A61M 5/326; A61M 5/3202; A61M 5/2033; A61M 25/02; A61M 25/0631; A61M 25/0637; A61M 2005/206; A61M 2005/327; A61M 2025/024

USPC ........... 604/162, 198, 164, 164.06, 171, 174, 604/192, 263, 177
See application file for complete search history.

(56) References Cited

U.S. PATENT DOCUMENTS 3,610,240 A   10/1971  Harautuneian
5,120,320 A *  6/1992  Fayngold ...................... 604/177
(Continued)

FOREIGN PATENT DOCUMENTS

DE     101 56 587 A1     5/2003
WO        90/03196 A1    4/1990
WO     2010/038844 A1    4/2010

OTHER PUBLICATIONS

International Search Report mailed on Mar. 18, 2011 for PCT Patent Application No. PCT/IB2010/054334, 3 pages.

*Primary Examiner* — Manuel Mendez
(74) *Attorney, Agent, or Firm* — Kilpatrick Townsend and Stockton LLP (57) ABSTRACT

The invention relates to a needle protector assembly (10) comprising a needle defining an axial direction and a protective cover for the needle. The needle is attached to a needle hub which is provided with wings on opposite sides thereof and which can be moved relative to the protective cover between a distal position in which at least a tip of the needle protrudes from the protective cover, and a proximal position in which the needle is fully received in the protective cover. The protective cover comprises first (26) and second parts (28) which together form an elongate housing along which the needle hub can move between the distal and proximal positions, wherein the first and second parts define elongate slots on opposite sides of the housing through which the wings (16) protrude.

11 Claims, 5 Drawing Sheets

(56) References Cited

U.S. PATENT DOCUMENTS

| | | | |
|---|---|---|---|
| 5,772,638 A * | 6/1998 | Utterberg et al. | 604/263 |
| 5,827,239 A * | 10/1998 | Dillon et al. | 604/263 |
| 7,060,055 B2 * | 6/2006 | Wilkinson et al. | 604/263 |
| 7,303,545 B2 * | 12/2007 | Sarstedt | 604/110 |
| 2003/0181874 A1 | 9/2003 | Bressler et al. | |
| 2004/0267200 A1 * | 12/2004 | Carlyon et al. | 604/110 |

* cited by examiner

NEEDLE PROTECTOR ASSEMBLY

CROSS-REFERENCES TO RELATED APPLICATIONS

This application is a U.S. National Phase under 35 USC 371 of PCT Application No. PCT/IB2010/054334 filed Sep. 27, 2010, which claims priority to the India Application No. 2124/DEL/2010, filed Sep. 7, 2010, the disclosures of which are incorporated by reference herein.

FIELD

The present invention relates to a needle protector assembly comprising a needle, for example of a disposable medical device, and a protective cover for the needle, wherein the needle is attached to a needle hub which can be moved relative to the protective cover between a distal position in which at least a tip of the needle protrudes from the protective cover, and a proximal position in which the needle is fully received in the protective cover.

A needle protector assembly of this kind is generally known and helps to prevent accidental contact of a medical professional or any other person with the tip of the needle after use of the disposable medical device. Such an accidental contact with a used needle can cause the transmission of a disease such as hepatitis, HIV, etc.

BACKGROUND

The increasing incidence of blood borne pathogens such as Human Immunodeficiency Virus (HIV), combined with Hepatitis B Virus (HBV) and Hepatitis C Virus (HCV), presents healthcare workers with an occupational hazard unprecedented in modern medicine. The risk of contracting HIV from a needle stick injury is approximately 1 in 100, but for those who contract HIV infection as a result of a needle stick injury the risk becomes 1 in 1. The risk of contracting the more contagious HBV as a result of a needle stick injury ranges from 1 in 6 to 1 in 20.

There are some other known blood borne pathogens which are transmitted via blood and bodily fluids. The presence of any of these pathogens in patients poses a risk to healthcare workers when invasive procedures are performed. Infectious diseases are now the third leading cause of death, behind heart disease and cancer, while ten years ago this was ranked fifth, signifying a growing need for safer medical devices.

As the population of infected individuals increases, more people will be treated by healthcare workers, which imposes further risks of disease transmission from patients to healthcare workers. Also, the use of disposable medical devices is increasing at approximately 10% per annum. Additionally, a remarkable number of patient to patient transmissions in the healthcare setting have been identified throughout the world. Early data suggests improper infection control techniques contribute directly to this increase: including improper use of medical devices having needles, multiple-dose medicine vials, and failure to change protective gloves and gear for each new patient.

Healthcare workers are increasingly at risk of disease transmission, and nurses perform the majority of invasive hypodermic procedures, such as injecting medicine, collecting blood and inserting indwelling intravenous (I.V.) catheters. Nurses and other healthcare personnel are routinely injured by the exposed, sharp lancet of the needle after use on a patient. The critical time where a percutaneous injury can occur is from the moment the needle is withdrawn from the patient, or I.V. port, to the time the contaminated needle is safely discarded.

Prior to the proliferation of HIV and serum hepatitis, a needle stick injury was considered a routine part of providing patient care. A needle stick injury now carries a life-threatening consequence and healthcare workers must live with this terror on a daily basis.

SUMMARY

It is an object of the invention to provide a needle protector assembly which provides reliable protection against accidental pricking by a needle, for example of a disposable medical device, and which is easy and inexpensive to manufacture.

This object is satisfied by a needle protector assembly having the features of a needle defining an axial direction and a protective cover for the needle, wherein the needle is attached to a needle hub which is provided with wings on opposite sides thereof and which can be moved relative to the protective cover between a distal position in which at least a tip of the needle protrudes from the protective cover, and a proximal position in which the needle is fully received in the protective cover, wherein the protective cover comprises first and second parts which together form an elongate housing along which the needle hub can move between the distal and proximal positions, wherein the first and second parts define elongate slots on opposite sides of the housing through which the wings protrude, and wherein the first and second parts are connected to one another by means of a film hinge in the region of a first axial end of the housing and by means of a latching mechanism in the region of a second axial end of the housing.

A needle protector assembly of the invention comprises a needle defining an axial direction and a protective cover for the needle. The needle is attached to a needle hub which is provided with wings on opposite sides thereof and which can be moved relative to the protective cover between a distal position in which at least a tip of the needle protrudes from the protective cover, and a proximal position in which the needle is fully received in the protective cover. The protective cover comprises first and second parts which together form an elongate housing along which the needle hub can move between the distal and proximal positions, wherein the first and second parts define elongate slots on opposite sides of the housing through which the wings protrude. The first and second parts are connected to one another by means of a film hinge in the region of a first axial end of the housing and by means of a latching mechanism in the region of a second axial end of the housing.

Examples of disposable medical devices in which the needle protector assembly can be used include, for example, devices which are used to collect blood from a patient or a donor or to give fluids to a patient, such as blood collection sets (PSV sets with luer adapters) and blood collection bag needles, scalp vein sets, and fistula needles. Typically, a PVC tube can be connected to the needle hub for the collection of blood drawn from a patient.

The film hinge allows for an integral production of the first and second parts and thus makes a less expensive production of the needle protector assembly possible. The arrangement of the film hinge in the region of an axial end of the housing simplifies the mounting of the protective cover on the needle and thus ultimately adds to decreased production costs. The film hinge may, for example, be formed from two links which are arranged on opposite sides of an opening at the axial end of the housing. Preferably, the first axial end of the housing is a distal end and the second axial end of the housing is a proximal end.

The latching mechanism also adds to the easy manufacturing of the needle protector assembly and may, for example, comprise at least one snap arm at one of the first and second parts for engagement with a respective latch opening in the respective other one of the first and second parts. Hence, the putting together of the protector cover and the needle simply requires arranging of the needle and needle hub in one of the first and second parts, folding over of the respective other one of the first and second parts, and snapping together of the first and second parts.

According to a preferred embodiment, the first and second parts form a tube-like housing portion for guiding the needle hub in the axial direction. The tube-like housing portion prevents the needle from sticking sideways out of the protective cover, thereby increasing the protective effect of the needle protector assembly.

Preferably, at least one of the first and second parts has an inner surface which defines a guide channel having a cross-section that is adapted to an outer profile of a portion of the needle hub. The guide channel prevents transverse and/or tilting movement of the needle hub and thus of the needle tip with respect to the axial direction, thereby improving correct functioning of the needle protector assembly and ultimately increasing the safety of the needle protector assembly even further.

According to a further embodiment, the first and second parts may form a flat housing portion in the region of a proximal end of the tube-like housing portion, the flat housing portion defining an internal passage, in which the needle hub is received when the needle hub is in the proximal position.

Preferably, the needle protector assembly comprises a locking mechanism adapted to secure the needle hub in the proximal position. The locking mechanism effectively prevents the needle from inadvertently protruding out of the protective cover at the distal end thereof. Thereby protection against accidental pricking by the needle is further increased. Consequently, the needle protector assembly of the invention ensures a safe disposal of the needle after its use.

According to an embodiment, the locking mechanism comprises a pair of first and second locking means engaging with each other when the needle hub is in the proximal position, wherein the first locking means is provided on the needle hub and the second locking means is provided on the protective cover.

The needle protector assembly is particularly inexpensive to manufacture, if the first locking means is formed integrally with the needle hub. Alternatively, the first locking means may be formed on a separate element, for example a ring, which is attached to the needle hub.

Preferably, the first locking means defines a surface facing the needle tip, wherein at least a portion of the surface extends in a plane generally perpendicular to the needle. This makes a particularly effective interaction between the first and second locking means possible.

According to a preferred embodiment, the first locking means comprises a protrusion protruding from the needle hub. For example, the first locking means may have a generally nose-like or ramp-like shape, with its radial dimension increasing towards the tip of the needle. The first locking means is preferably arranged in the region of a proximal end of the needle hub.

Furthermore, the first locking means may be formed such that a radial dimension of the locking means can be reduced against a restoring force. For example, the first locking means may be formed from a material having elastic properties. This may facilitate the movement of the needle hub into an interior passage of the protective cover.

According to a further embodiment, the second locking means comprises an opening, for example a slot, in the protective cover, which is adapted to receive the first locking means when the needle hub is in the retracted position. A second locking means in the form of an opening in the protective cover is particularly advantageous, if the first locking means is formed from a protrusion protruding from the needle hub and having elastic properties, such that it can engage in the opening if correctly positioned, thereby interlocking the needle hub and the protective cover.

Additionally or alternatively, the second locking means may comprise a locking tongue extending towards a proximal end of the protective cover and adapted to engage with the first locking means, when the needle hub is in the retracted position.

Preferably, the locking tongue has resilient properties and extends towards the interior of the protective cover, such that it is pushed outwards by the first locking means as the needle hub is moved towards its proximal position, and snaps back behind the first locking means once the needle hub has adopted its proximal position. In the case of such a resilient locking tongue, a first locking means in the form of a protrusion protruding from the needle hub may have elastic properties; however, this is not compulsory.

The cost for the production of the needle protector assembly can be further decreased, if the locking tongue is integrally formed with the protective cover.

BRIEF DESCRIPTION OF THE DRAWINGS

Preferred embodiments of the invention are described in the following description and in the accompanying drawings, wherein.

DETAILED DESCRIPTION

Figure 1:
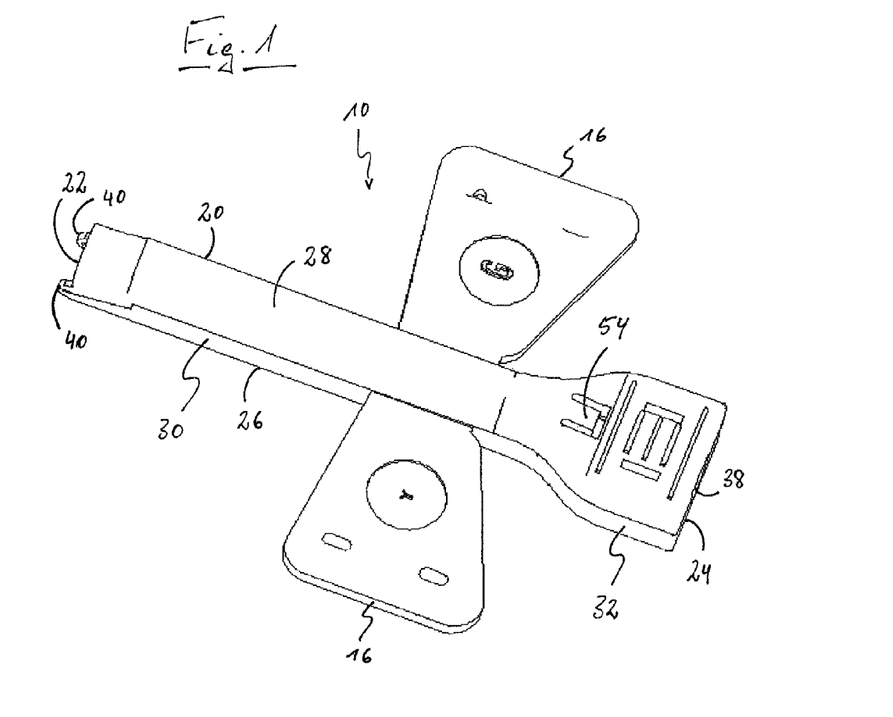
FIG. 1 is a perspective view of a top side of a needle protector assembly of the invention, wherein a needle hub of the assembly is in a proximal position.
Figure 2:
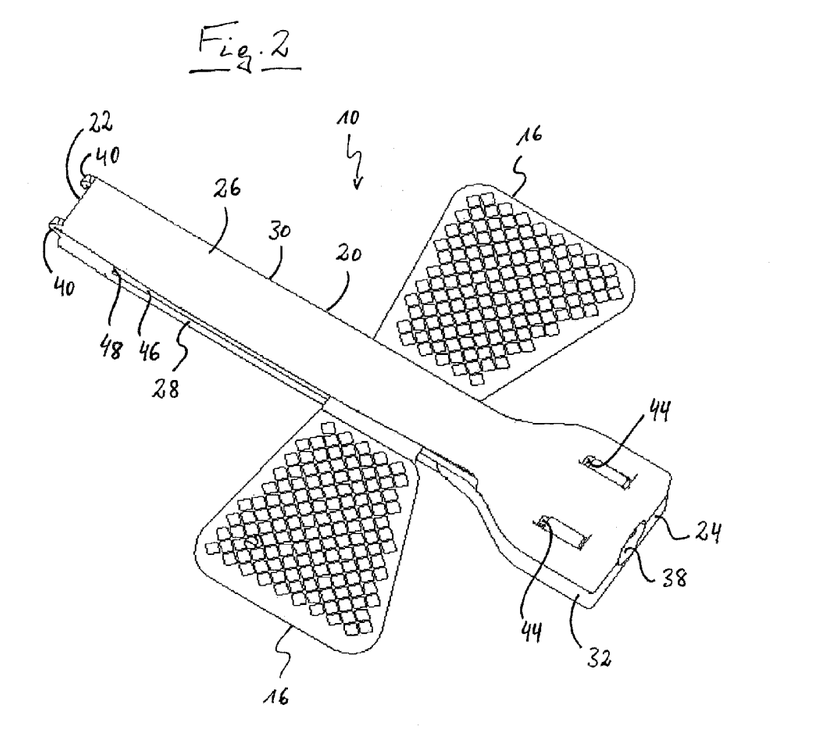
FIG. 2 is a perspective view of a bottom side of the needle protector assembly of FIG. 1.

FIGS. 1 and 2 illustrate a needle protector assembly 10 according to the invention. The needle protector assembly 10 is part of a disposable medical device, for example a blood collection kit, having a hypodermic needle (not shown) and is provided to prevent accidental contact of a medical professional or any other person with the sharp tip of the needle after use of the disposable medical device.

In this context, the end of the needle having the sharp tip is denoted the distal end, whereas the opposite end of the needle is denoted the proximal end. Likewise the orientation of parts of other structural elements facing towards the needle tip will be referred to as distal, whereas the orientation of parts of these structural elements facing in the opposite direction will be referred to as proximal.

The needle extends in an axial direction, thereby defining an axial direction for the needle protector assembly 10. A direction perpendicular to the axial direction is denoted as radial.

In the region of its proximal end the needle is connected to a needle hub. The needle hub comprises a tubular main body (not shown) and two wings 16 which extend in opposite radial directions from the main body. The wings 16 can either be formed integrally with the main body, or they can be separate elements that are attached to the main body.

A PVC tube (not shown) can be attached, for example glued, to a proximal end portion of the main body of the needle hub. The other end of the PVC tube may, for example, be connected to a blood collection bag (not shown) or any other component to facilitate flow of fluid, such as medicine or blood, to or from a patient or donor.

The needle protector assembly 10 further comprises a protective cover 20 generally extending in the axial direction and having a distal end 22 and a proximal end 24. The needle hub is slidably arranged in the protective cover 20 such that the needle hub can be moved from a distal position, in which the sharp tip of the needle protrudes from the protective cover 20, to a proximal position, in which the needle is completely received in the protective cover 20.

The protective cover 20 comprises a first part 26, also referred to as the bottom part, and a second part 28, also referred to as the top part. The first and second parts 26, 28 together form a tube-like housing portion 30 for guiding the needle hub in the axial direction. At its proximal end the tube-like housing portion 30 widens into a flat housing portion 32.

Figures 3, 4:
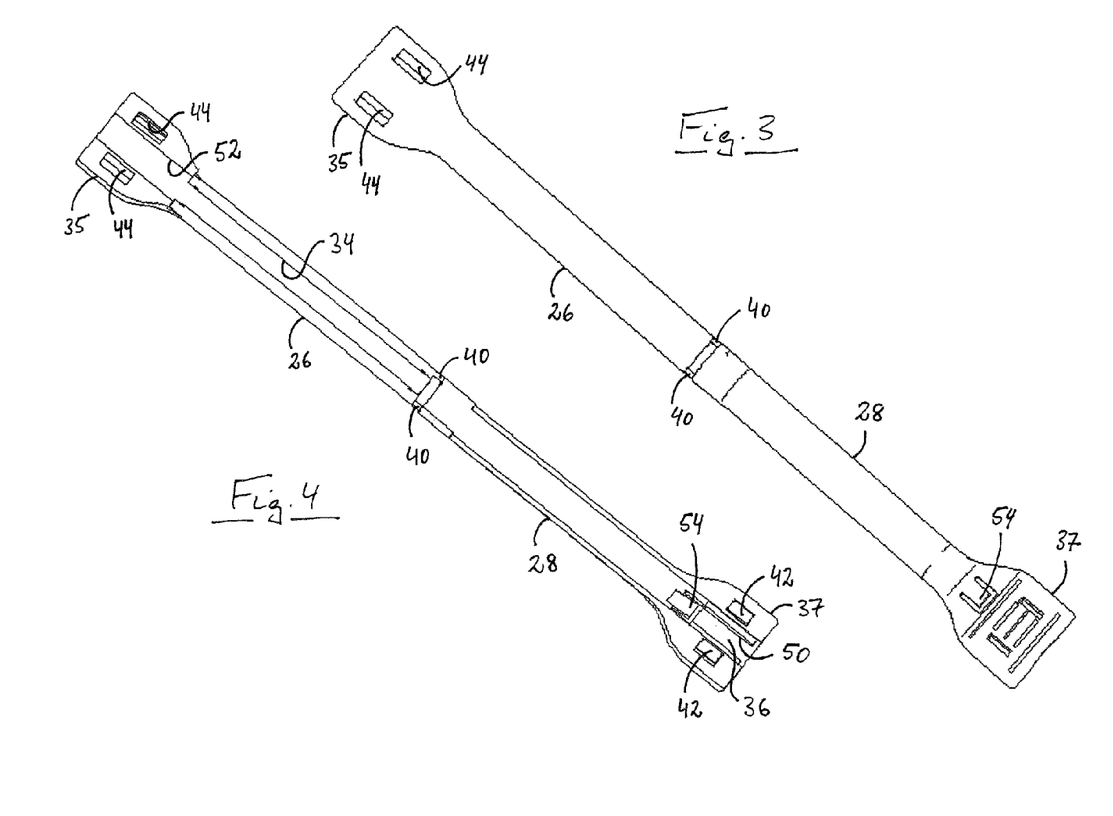
FIG. 3 is a perspective view of the outside of a protective cover of the needle protector assembly of FIG. 1 in a pre-assembled state.
FIG. 4 is a perspective view of the inside of the protective cover of FIG. 3.

As shown in FIG. 3, the section of the bottom part 26 forming the tube-like housing portion 30 has a generally rectangular outer profile with a planar bottom surface. As shown in FIG. 4, the inner surface of the bottom part 26 defines a guide channel 34 having a cross-section that is adapted to an outer profile of a portion of the needle hub. In contrast thereto, the section of the top part 28 forming the tube-like housing portion 30 is generally shaped as a half tube.

The guide channel 34 of the bottom part 26 extends through the widened section 35 of the bottom part 26 defining the flat housing portion 32, and a corresponding guide channel 36 is formed in the widened section 37 of the top part 28. Thus, an internal passage 38 is defined in the flat housing portion 32 of the assembled protective cover 20, through which the PVC tube extends when the needle hub is in its distal position and in which a portion of the needle hub is received, when the needle hub is in its proximal position.

At the distal end 22 of the protective cover 20, the bottom part 26 and the top part 28 are connected to one another by means of two bridges or links 40 arranged on opposite sides of an opening for the needle. The links 40 together form a film hinge which makes it possible to fold the bottom and top parts 26, 28 onto one another from a pre-assembled state (shown in FIGS. 3 and 4) to an assembled state (shown in FIGS. 1 and 2).

The bottom part 26, the top part 28 and the two links 40 are formed as an integral part, for example, as an injection molded plastic part.

In the region of the flat housing portion 32, the bottom part 26 and the top part 28 are secured to one another by means of a latching mechanism. The latching mechanism comprises two snap arms 42 provided at the top part 28 on opposite sides of the guide channel 36, and two respective latch openings 44 on opposite sides of the guide channel 34 in the bottom part 26 for receiving the snap arms 42.

In the assembled state of the needle protector assembly 10, sidewalls of the bottom part 26 and the top part 28 define elongate slots 46 on opposite sides of the protective cover 20, through which the wings 16 of the needle hub protrude. The slots 46 have a smooth and generally straight form, i.e. they do not define any obstacles that could interfere with a free movement of the wings 16 along the slots 46 and, thus, with a free movement of the needle hub along the tube-like housing portion 30 of the protective cover 20.

Distal ends of the slots 46 are defined by steps 48 in the sidewalls of the top part 28.

An axially extending wall 50 partly defining the internal passage 38 in the flat housing portion 32 protrudes from the widened section 37 of the top part 28 and engages an associated recess 52 formed in the bottom part 26 in the assembled state of the needle protector assembly 10. The wall 50 thus defines a proximal end of the slots 46 and thereby limits movement of the needle hub in the proximal direction once the needle hub reaches its proximal position.

In order to secure the needle hub in its proximal position the needle protector assembly 10 comprises a locking mechanism.

Figure 5A:
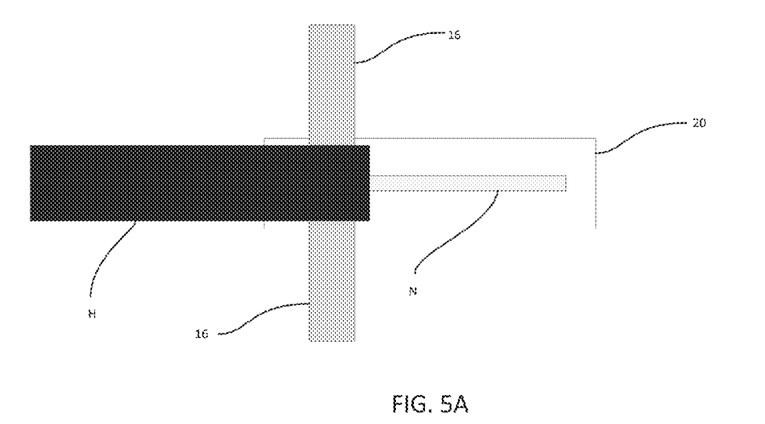
FIG. 5A shows a needle hub H proximal position. The need hub H being part of a needle protector assembly of the invention which comprises a needle N defining an axial direction and a protective cover 20 for the needle N. The needle N is attached to a needle hub H which is provided with wings 16 on opposite sides thereof and which can be moved relative to the protective cover 20 between a distal position in which at least a tip of the needle N protrudes from the protective cover 20, and a proximal position in which the needle N is fully received in the protective cover 20.
Figure 5B:
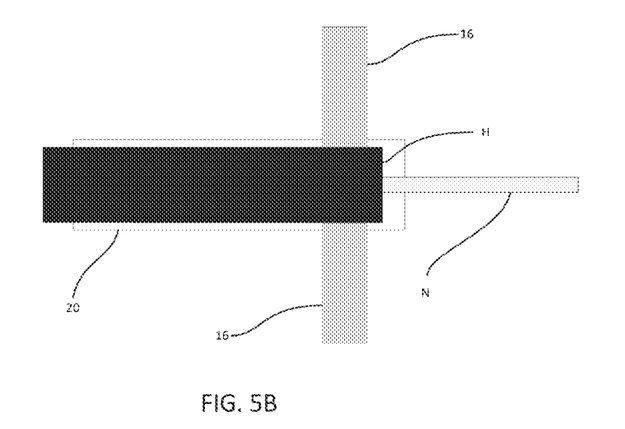
FIG. 5B shows a needle hub H proximal position in which the needle N is fully received in the protective cover 20.
Figure 5C:
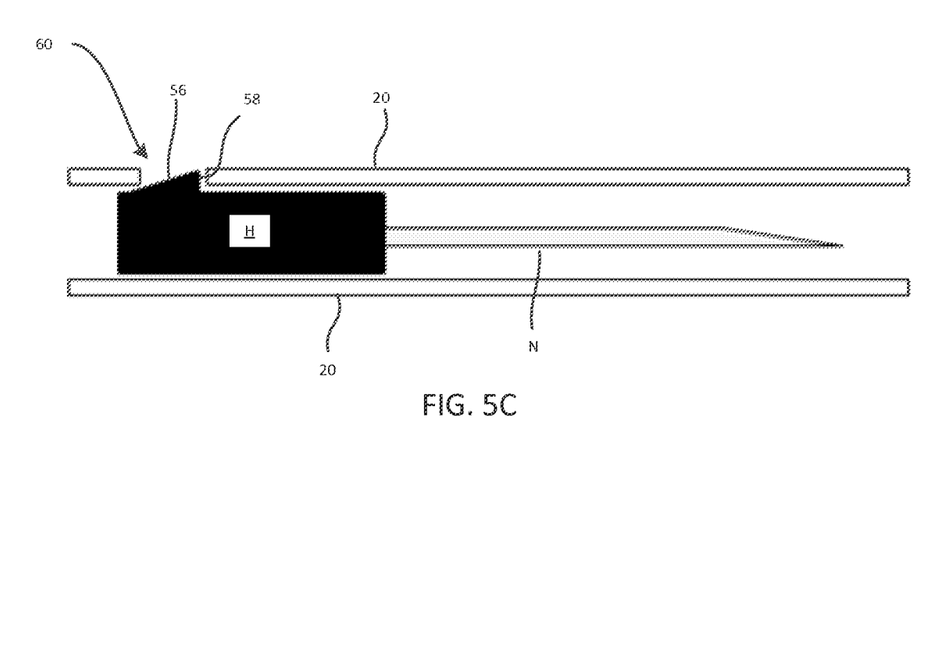
FIG. 5C shows an exemplary locking mechanism of a needle protector assembly.

The locking mechanism includes a locking protrusion 56 arranged on a top side of the main body of the needle hub H in a proximal region thereof, (FIG. 5C). The locking protrusion 56 is integrally formed with the main body and has a generally nose-like or ramp-like shape, with its radial dimension increasing towards the tip of the needle N. A distal surface 58 of the locking protrusion 56 facing the needle tip extends in a plane generally perpendicular to the axial direction.

According to a further embodiment, the second locking means comprises an opening 60, for example a slot, in the protective cover 20, which is adapted to receive the first locking means when the needle hub H is in the retracted position. A second locking means in the form of an opening 60 in the protective cover 20 is particularly advantageous, if the first locking means is formed from a protrusion 56 protruding from the needle hub H and having elastic properties, such that it can engage in the opening 60 if correctly positioned, thereby interlocking the needle hub H and the protective cover 20.

The locking mechanism further includes a locking tongue 54 provided on the top part 28 in the region of transition from the tube-like section to the widened section 37. The locking tongue 54 is integrally formed with the top part 28 and has resilient properties. The locking tongue 54 is aligned with the internal passage 38 and extends towards the proximal end of the protective cover 20 and into the internal passage 38 (FIG. 4).

Generally, the locking tongue 54 may have different shapes. However, a compulsory requirement is that the locking tongue 54 needs to be shaped such that its free end abuts against the distal surface of the locking protrusion facing the needle tip when the needle is fully received in the protective cover 20.

The function of the needle protector assembly 10 is as follows:

Prior to use of the assembled needle protector assembly 10 the needle hub is in its distal position, also referred to as a position of use.

A medical professional holds the wings 16 attached to the needle hub and punctures the skin of a patient with the needle such that the needle enters a vein of patient. As the needle enters the vein, blood rushes into the needle and through the main body of the needle hub into the PVC tube. The blood is collected in a blood collection bag or a vacuum tube through a connection to the other end of the PVC tube. Alternatively, the device may be used to give fluids or medications to a patient.

After a required quantity of blood has been collected, the needle is withdrawn from the vein by holding the wings 16. As the needle is pulled out of the patient, it enters the protective cover 20. At the same time the needle hub moves backwards towards the flat housing portion 32.

When the needle hub moves towards its proximal position, the locking protrusion of the needle hub engages with the locking tongue 54 of the protective cover 20. The locking tongue 54 runs up the sloped side of the locking protrusion and is thereby pushed outward.

Once the needle hub has adopted its proximal position in which the needle is fully received in the protective cover 20, the locking protrusion has passed the locking tongue 54 such that the locking tongue 54 snaps back inside due to its resilient properties and engages behind the locking protrusion, thereby preventing movement of the needle hub towards the distal end 22 of the protective cover 20.

Hence, in the proximal position of the needle hub, the needle is safely locked inside the protective cover 20 and the blood collection set can be safely disposed of without danger of the needle pricking any person.

The invention claimed is:

1. A needle protector assembly comprising a needle defining an axial direction and a protective cover for the needle,
wherein the needle is attached to a needle hub which is provided with wings on opposite sides thereof and which can be moved relative to the protective cover between a distal position in which at least a tip of the needle protrudes from the protective cover, and a proximal position in which the needle is fully received in the protective cover,
wherein the protective cover comprises first and second parts which together form an elongate housing along which the needle hub can move between the distal and proximal positions,
wherein the first and second parts define elongate slots on opposite sides of the housing through which the wings protrude, and
wherein the first and second parts are connected to one another by a film hinge in the region of a first axial end of the housing and by a latching mechanism in the region of a second axial end of the housing;
wherein a locking mechanism is provided which is adapted to secure the needle hub in the proximal position, wherein the locking mechanism comprises a pair of first and second locking means engaging with each other when the needle hub is in the proximal position, wherein the first locking means is provided on the needle hub and the second locking means is provided on the protective cover, and wherein the first locking means is formed such that a radial dimension of the first locking means is reduceable against a restoring force;
wherein the first locking means has a ramp-like shape with the radial dimension increasing towards the tip of the needle;
wherein the second locking means comprises an opening in the protective cover which is adapted to receive the first locking means when the needle hub is in the proximal position.

2. The needle protector assembly in accordance with claim 1, wherein the film hinge is formed from two bridges or links which are arranged on opposite sides of an opening at an axial end of the housing.

3. The needle protector assembly in accordance with claim 1, wherein the first axial end of the housing is a distal end and the second axial end of the housing is a proximal end.

4. The needle protector assembly in accordance with claim 1, wherein the first and second parts form a tube-like housing portion for guiding the needle hub in the axial direction.

5. The needle protector assembly in accordance with claim 1, wherein at least one of the first and second parts has an inner surface which defines a guide channel having a cross-section that is adapted to an outer profile of a portion of the needle hub.

6. The needle protector assembly in accordance with claim 1, wherein the first and second parts form a flat housing portion in the region of a proximal end of the tube-like housing portion, the flat housing portion defining an internal passage in which the needle hub is received when the needle hub is in the proximal position.

7. The needle protector assembly in accordance with claim 1, wherein the latching mechanism comprises at least one snap arm at one of the first and second parts for engagement with a respective latch opening in the respective other one of the first and second parts.

8. The needle protector assembly in accordance with claim 1, wherein the first locking means is formed integrally with the needle hub.

9. The needle protector assembly in accordance with claim 1, wherein the first locking means is formed from a material having elastic properties.

10. The needle protector assembly in accordance with claim 1, wherein the second locking means comprises a locking tongue extending towards a proximal end of the protective cover and adapted to engage with the first locking means, when the needle hub is in the proximal position.

11. The needle protector assembly in accordance with claim 10, wherein the locking tongue has resilient properties and extends towards the interior of the protective cover such that it is pushed outwards by the first locking means as the needle hub is moved towards its proximal position, and snaps back behind the first locking means once the needle hub has adopted its proximal position.

* * * * *